United States Patent [19]

Conley et al.

[11] Patent Number: 5,106,728

[45] Date of Patent: Apr. 21, 1992

[54] CALLIER DIAGNOSTIC METHOD FOR AGAMMAGLOBULINEMIA AND CARRIER SCREENING METHOD FOR X LINKED SEVERE COMBINED IMMUNODEFICIENCY

[75] Inventors: Mary E. Conley, Philadelphia; Robert L. Nussbaum; Jennifer M. Puck, both of Ardmore, all of Pa.

[73] Assignees: Childrens Hospital of Philadelphia; Trustees of the University of Pennsylvania, both of Philadelphia, Pa.

[21] Appl. No.: 494,942

[22] Filed: Mar. 14, 1990

Related U.S. Application Data

[63] Continuation of Ser. No. 881,624, Jul. 3, 1986, abandoned.

[51] Int. Cl.$^5$ .................. C12Q 1/68; A01N 63/00
[52] U.S. Cl. ............................................ 435/6; 436/811
[58] Field of Search .......................... 435/6; 424/93

[56] References Cited

PUBLICATIONS

Harley et al., Pediat Res 15 (1981) 596.
Migeon B. R. in *Genetic mosaics and chimeras in mammals* New York: Plenum (1978) 417–32.
Windhorst et al., Lancet (1967) 1 737–9.
Fialkow, Philip J., "Primordial Cell Pool Size and Lineage Relationships of Five Human Cell types", Ann. Hum. Genet., Lond. (1973) 37: pp. 39–48.
Maniatis, et al., Molecular Cloning, A Laboratory Manual, Cold Spring Harbor Laboratory, Cold Spring Harbor, New York, (1982) pp. 382–389.
Nyhan, et al., (1970) Proc. Natl Acad. Sci. USA vol. 65, pp. 214–218.
Gealey et al., "Oleic Exclusion of Glucose-6-Phosphate Dehydrogenase in Platelets and T Lymphocytes form a Wiscott-Aldrich Syndrome Carrier", The Lancet, pp. 63–65 (Jan. 12, 1980).
Prchal et al., "Wiskott-Aldrich Syndrome: Cellular Impairments and Their Implications for Carrier Detection", Blood 56 (6): 1048–1054 (1980).
Migeon et al, "Adrenoluekodystrophy: Evidence for X Linkage, Inactivation, and Selection Favoring the Mutant Allele in Heterozygous Cells", Proc. Natl. Acad. Sci., 78: 5066p14 5070 (1981).
Wieaker et al, "X Inactivation Patterns in Two Syndromes With Probable X-Linked Cominant, Male Letal Inheritance", Clinical Genetics, 28: 238–242 (1985) (Sep. 1985 cover date.
Nussbaum et al., "A Three-Allele Restriction-Fragment-Length Polymorphism at the Hypoxanthine Phosphoribosyltransferase Locus in Man", Proc. Nat. Acad. Sci. USA, 80: 4035–4039 (Jul., 1983).
Fogelstein et al, "In Use of Restriction Fragment Length Polymorphisms to Determine the Clonal Origin of Human Tumors", Science, 227: 642–645 (Feb. 8, 1985).

Bruton, "Agammaglobulinemia", Pediatrics, 9:722–28 (1952).
Conley, "B Cells in Patients With X-Linked Agammaglobulinemia", J. of Immunol., 134: 3070–3074 (1985).
Pearl et al, "B Lymphocyte Precursors in Human Bone Marrow: An Analysis of Normal Individuals and Patients With Antibody-Deficient States", J. of immunoL, 102: 1169–1175 (1978).
Conley et al, "In Vitro Regulation of IgA Subclass Synthesis, II the Source of IgA$_2$ Plasma Cells", J. of Immunol., 133: 2312–2316 (1984).
Singer et al, "Single or Multicellular Origin of Human T Lymphocyte Colonies in Vitro; Modification by 12-0-Tetradecanoylphorbol 13-Acetate (TPA)", J. of Immunol. 126: 1390–1392 (1981).
Raskind et al, "Evidence for a Multistep Pathogenesis of Myelodysplastic Syndrome", Blood, 63: 1318–1323 (1984).
Yoshida et al, "Negro Variant of Blucose-6-Phosphate Dehydrogenase Deficiency (A$^-$) in Man", Science, 155: 97–99 (1967).
Tedder et al, "Evaluation of Lymphocyte Differentiation in Primary and Secondary Immunodeficiency Diseases", J. of Immunol., 135:1786–1791 (1985).
Thompson et al, "Ecto-5' -Nucleotidase Activity in Lymphoblastoid Cell Lines Derived from Heterozygotes for Congential X-Linked Agammaglobulinemia", J. of Immunol., 125: 190–193 (1980).
Sanger et al, "The Xg Blood Groups and Familial Hypogammaglobulinemia", Lancet, 1:859–860 (1963).
Rosen et al, "The Xg Groups and Congential Hypogammaglobulinemia," Vox Sang., 10: 729–730 (1965).
Mensink et al, "X-Linked Agammaglobulinemia and the Red Blood Cell Determinants Xg and 12E7 Are Not Closely Linked, Hum. Genet.", 68: 303–309 (1984).

(List continued on next page.)

Primary Examiner—Robert A. Wax
Assistant Examiner—S. Chambers
Attorney, Agent, or Firm—Woodcock Washburn Kurtz Mackiewicz & Norris

[57] ABSTRACT

There is provide by the invention a method of diagnosing a human female suspected of being an symptomatic carrier of X-linked agammaglobulinemia (XLA). The method comprises sampling B cell lymphocytes of said female; and determining whether at least 95% of said B cell lymphocytes exhibit inactivation of the same chromosome; whereby said X chromosome inactivation is diagnostic of XLA. The invention further provides a method of screening a human female suspected of being an asymptomatic carrier of X-linked severe combined immunodeficiency (XSCID). The method comprises sampling the B or T cell lymphocytes of said female; determining whether at least 85% of said lymphocytes exhibit inactivation of the same chromosome; whereby said X chromosome inactivation is associated with XSCID.

12 Claims, No Drawings

PUBLICATIONS

Schuurman et al, "X-Linked Agammaglobulinemia: Mapping of the Gene for XLA Carrier Detection", *Ped. Res.*, 19:1072 (Abstract) (1985).

Belmont et al, "Regional Mapping of X-Linked Agammaglobulinemia", *Am. J. Human Gen.*, 37: A140 (Abstract) (1985).

Mohandas et al, "Reactivation of an Inactive Human X Chromosome: Evidence for X Inactivation by DNA Methylation", *Science,* 211:393–396 (1981).

Fearon et al, "Carrier Detection In X-Linked Agammoglobulinemia by Analysis of X-Chromosome Inactivation", *New England Journal of Medicine,* 316, No. 8, p. 427 (Feb. 19, 1987).

CALLIER DIAGNOSTIC METHOD FOR AGAMMAGLOBULINEMIA AND CARRIER SCREENING METHOD FOR X LINKED SEVERE COMBINED IMMUNODEFICIENCY

This is a continuation of application Ser. No. 881,624, filed Jul. 3, 1986, now abandoned.

BACKGROUND OF THE INVENTION

The present invention relates to the field of tests and/or method for identifying asymptomatic carriers of X-linked immunodeficiencies. More particularly, it relates to methods for identifying asymptomatic carriers of agammaglobulinemia (XLA), severe combined immunodeficiency (XSCID). It also relates to immunoproliferative syndrome (XLP), Wiscott-Aldrich syndrome (WAS) and hyper-IgM syndrome.

While for some genetic diseases, heterozygous carriers can be identified by laboratory tests or specific findings on physical examination, there are many diseases in which carriers appear to be normal in all respects. Such is the case with most X-linked immunodeficiencies, including XLA, XSCID, XLP, WAS, and hyper-IgM syndrome. A carrier detection test would be extremely valuable for both family counseling and planning medical treatment, including bone marrow transplantation, of potentially affected off-spring. Furthermore, knowledge of carrier status in affected pedigrees would greatly facilitate gene mapping, and ultimately cloning of the genes responsible for these diseases. At the present time, no reliable carrier detection tests for these diseases are available.

In order to learn more about X-linked genetic defects of various types, a number of researchers have investigated such defects using existing genetic markers such as G6PD isoenzymes. These researchers have sought those rare individuals who are both heterozygous for G6PD, and for the defect under investigation. When the carrier of a recessive genetic defect appears normal, G6PD may be used to determine which X chromosome is active in the cells under investigation. The use of G6PD isoenzymes as a genetic marker is based upon the Lyon hypothesis which states that random inactivation of one or the other of the two X chromosomes in each female cell occurs during embryonic development. As a consequence, the Lyon hypothesis teaches that the human female is a mosaic, that is, only one X chromosome or the other is expressed in each cell.

Evidence exists that non-random X chromosomal representation occurs in particular cell-types in carriers of diseases such as Wiscott-Aldrich syndrome. Gealey et al, "Oleic Exclusion of Glucose-6-Phosphate Dehydrogenase in Platelets and T Lymphocytes from a Wiscott-Aldrich Syndrome Carrier", *The Lancet*, pp. 63-65 (Jan. 12, 1980). Gealey et al reports that non-random X inactivation occurs in WAS carriers in certain tissue lineages, particularly T lymphocytes. Gealey et al conclude that normal random X inactivation is followed by separate WAS-defect-dependent selection events occurring in post-thymus lymphocytes and platelets or platelet precursors. However, Gealey et al suggest that this hypothesis is not necessarily consistent with all of the available observations, at least as to expressed abnormalities in secondary platelet aggregation. See also Prchal et al, "Wiskott-Aldrich Syndrome: Cellular Impairments and Their Implications for Carrier Detection", *Blood* 56(6):1048-1054 (1980).

G6PD has also been used to determine whether skin related defects may be X-linked. G6PD has thus been employed to study heterozygous defects wherein selection may favor the mutant allele in vivo. See Migeon et al, "Adrenoluekodystrophy: Evidence for X Linkage, Inactivation, and Selection Favoring the Mutant Allele in Heterozygous Cells", *Proc. Natl. Acad. Sci.*, 78:5066-5070 ((1981).

Nyhan et al., (1970) *Proc. Natl. Acad. Sci USA* 65: 214-218, have suggested either that subjects heterozygous for the Lesch-Nyhan syndrome (a deficiency of the X linked gene for the enzyme hypoxanthine-guanine phosphoribosyl transferase (PRT)) undergo inactivation of the X chromosome that is not random or that random X chromosome inactivation is followed by selection against erythrocyte precursors with the mutant enzyme. Females heterozygous at the G6PD locus and the PRT locus were found to exhibit only one form of G6PD in circulating erythrocytes, thereby providing evidence supportive of this hypothesis.

Of course, genetic defects may or may not be related to non-random X chromosome inactivation. In "X Inactivation Patterns in Two Syndromes with Probable X-Linked Dominant, Male Lethal Inheritance", by Wieaker et al, *Clinical Genetics*, 28:238-242 (1985) (Sept., 1985 cover date; received University of Pennsylvania Library, Nov. 13, 1985) X inactivation patterns for two defects found only in females, incontinentia pigmenti (IP) and Aicardi syndrome, was hypothesized. IP is a rare skin condition; Aicardi syndrome is a symptomatically diagnosable condition. Preferential inactivation of the X chromosome carrying the IP gene with a proliferative advantage of the cell population was suggested, and partially supported by showing that the same X chromosome is preferentially active in fibroblasts grown from normal and hyperpigmented skin of a girl with IP, but not in a girl with Aicardi syndrome. Wieaker et al cultured fibroblasts grown from normal and hyperpigmented skin of the girl with IP and fused with HPRT-deficient mouse RAG cells according to a standard polyethylene glycol fusion protocol. Hybrids were selected and isolated and analyzed for an X-linked restriction fragment length polymorphism for which she was known to be heterozygous. The probe was thus employed to distinguish the two chromosomes of the patient and to determine the identity of the human X chromosomes retained in somatic cell hybrids. The results were said to demonstrate unambiguous evidence for preferential X chromosome activity in the IP patient, suggesting that there was somatic selection against cells that expressed the IP gene.

Somatic cell hybrids have also been used with Southern blotting and restriction-fragment-length polymorphisms (RFLPs) to investigate X-linked defects of Lesch-Nyhan syndrome patients. Nussbaum et al, "A Three-Allele Restriction-Fragment-Length Polymorphism at the Hypoxanthine Phosphoribosyltransferase Locus in Man", *Proc. Nat. Acad. Sci. USA*, 80:4035-4039 (July, 1983). This paper, which is co-authored by one of the inventors hereof, is hereby incorporated by reference. It is of particular pertinence for its disclosure of materials and methods relating to cell lines, somatic hybrid studies and its preparation of DNA and Southern blotting experiments.

For other purposes, it is sometimes desirable to distinguish active from inactive X chromosomes. Fogelstein et al, "In Use of Restriction Fragment Length Polymorphisms to Determine the Clonal Origin of Human Tumors", *Science*, 227:642-645 (Feb. 8, 1985), report the use of two restriction endonucleases to distinguish active from inactive copies of a gene. This strategy was used to demonstrate that three human cancers were each monoclonal.

Although X-linked agammaglobulinemia (XLA) was one of the first immunodeficiencies described, the genetic defect responsible for this disorder has not yet been identified. See Bruton, "Agammaglobulinemia", *Pediatrics*, 9:722-28 (1952). XLA is characterized by the onset of recurrent bacterial infections in the first few years of life. Concentrations of serum immunoglobulins are markedly decreased and the number of B cells present in the peripheral circulation of affected males is less than one percent of normal. However, pre-B cells, the non-circulating precursors of B cells, (Conley, "B Cells in Patients with X-Linked Agammaglobulinemia", *J. of Immunol.* 134:3070-3074 (1985)) can be detected in the bone marrow of affected individuals in approximately normal numbers (Pearl et al, "B Lymphocyte Precursors in Human Bone Marrow: An Analysis of Normal Individuals and Patients with Antibody-Deficient States", *J. of Immunol.*, 120:1169-1175 (1978)).

Congenital severe combined immunodeficiency (SCID) has a male to female ratio of 4 to 1, implying that 60% of the cases are caused by a gene defect on the X chromosome. SCID is known to result in abnormalities in both T and B cell immunity, but the nature of the defect at the gene level is entirely obscure. From the point of view of genetic counseling, it is unfortunate that even though the X linked form is by far the most common form of SCID, all XSCID carrier mothers have a completely normal phenotype, and no carrier detection tests are currently available.

Although much is known about the clinical course of patients suffering from X-linked immunodeficiencies, a need still exists for a reliable screening test for asymptomatic XLA and XSCID carriers who are impossible to detect using normal immunological techniques.

SUMMARY OF THE INVENTION

The present invention provides a novel approach for determining whether an asymptomatic female is a carrier of XLA or XSCID. It has been found for these diseases that early in the embryogenesis of the female, non-random inactivation of one of the X chromosomes occurs in each symptomatic cell and is transmitted to all descendents of that cell in accordance with the Lyon hypothesis. Thus, on average, it has been determined that carriers of XLA and XSCID have certain cell lineages which represent exceptions to the normal mosaicism which otherwise results in half the cells in every tissue using each X chromosome as the active X. In this respect, these lineages of XLA or XSCID carriers are similar to monoclonal malignancies or to tissues where a selective advantage of cells expressing the genes on one X chromosome over cells expressing genes on the others is present.

The completely normal immunological findings in women who are obligate carriers of X linked immunodeficiencies such as XLA or XSCID is thus explained by the fact that the cell lineage affected by the gene defect, B lymphocyte cell lineage in XLA and B and T lymphocyte cell lineages in XSCID, uses only the X chromosome that does not carry the defective gene as the active X chromosome.

Accordingly, a method of diagnosing for either XLA or XSCID X-linked genetic defects in a female suspected by pedigree of being an asymptomatic heterozygous carrier of one of those defects is provided which comprises the steps of sampling the B and/or T cell lymphocyte lineage(s) of said female; determining whether such cell lineage exhibits a non-random X chromosome inactivation, and diagnosing that the suspected female is a carrier based upon a determination that non-random X chromosome inactivation is present in the tested lymphocyte lineage. By testing both B and T cells, carriers of XLA (who are normal for T cells) can be distinguished from those of XSCID (who are non-random for both).

It is also believed that the techniques of the present invention may be applicable to screen for asymptomatic carriers of certain other X-linked genetic defects. This method includes identifying a cell lineage in which the genetic defect is likely to result in a selective cellular disadvantage in the asymptomatic heterozygous female; analyzing said cell type in a known heterozygous carrier to confirm non-random X chromosome inactivation in such cell lineage; testing said cell lineage of said female to determine whether such cell type exhibits similar non-random X chromosome inactivation, whereby the determination of such similar non-random X chromosome inactivation indicates a probability of said female being a carrier of said defect. In this general method, the step of analyzing the cell type of a known heterozygous carrier comprises the step of determining the frequency of occurrence of each active X allele in said cell lineage of said carrier, preferably by determining the frequency of occurrence of each active X allele in a normal cell type of that carrier and comparing that frequency to the frequency of each active X allele in the affected cell lineage of that carrier, whereby differences in those frequencies are indicative of the degree of non-random X chromosome inactivation in that lineage. Similarly, the testing step for the suspected female carrier comprises the steps of determining the frequency of occurrence of each active X allele in said cell lineage of said female, and comparing the frequency of that occurrence to the frequency of the occurrence of each active X allele in a normal cell lineage of said carrier, differences in said frequencies being indicative of degree of non-random X chromosome inactivation.

In accordance with this general method, the step of determining for non-random X chromosome inactivation may further comprise identifying an X chromosome marker in the female and testing for the frequency of that X chromosome marker in the cell lineage of said female. A second X linked heterozygous allele, such as an X linked heterozygous allele of G6PD is presently preferred, however other known biochemical or antigenic X chromosome markers may also be used.

The method of the present invention is expected to be useful in identifying asymptomatic carriers of immunoproliferative syndrome (wherein the tested cell lineage is either B or T cell lymphocytes); Wiscott-Aldrich syndrome (wherein the tested cell lineage is T lymphocytes); and hyper-IgM syndrome (wherein the tested cell lineage is either B or T cell lymphocytes).

The preferred method for testing a cell lineage to determine whether that lineage exhibits a non-random X chromosome inactivation comprises separating active X chromosomes from inactive X chromosomes by forming a hybrid with a mammalian somatic cell line from which a critical gene, such as the gene for HPRT, has been deleted. The resultant hybrid cell line may be grown in monoclonal populations in media which select for (or against) hybrids which have active human X chromosomes. Through the use of restriction fragment length polymorphisms and the Southern blotting technique, such hybrids may be analyzed to determine whether one or both X chromosomes are active in the subject cell lineage. When the lineage from which the hybrid is formed is a B cell lineage of a heterozygous carrier for XLA, all hybrids (having only one human X chromosome) will have the same X chromosome as its active human X. Similarly, XSCID carriers will yield hybrids revealing that the same X chromosome is the active X in all hybrids.

The present invention thus provides a method which is able to predict the carrier status for every woman who is suspected by pedigree evaluation of being a carrier of these relatively rare defects. It uses peripheral blood, a readily available tissue and has a very high degree of accuracy. Although the test is now relatively expensive and time consuming because of its use of sophisticated fusion, culture, restriction and blotting procedures, it is anticipated that progress in allied disciplines may substantially reduce the time and expense involved in screening large number of patients using these techniques.

Accordingly, a primary object of the present invention is the provision of a reliable carrier detection test for asymptomatic X-linked immunodeficiencies including XLA and XSCID.

These and other objects of the present invention will become apparent from the following more detailed description.

DESCRIPTION OF THE PREFERRED EMBODIMENTS

The present invention provides a novel approach for determining whether an asymptomatic female is a carrier of XLA or XSCID. It also provides a method which may be useful in several other X-linked genetic diseases. The test is based upon the hypothesis that the completely normal immunologic findings in women who are obligate carriers of most X-linked immunodeficiencies is explained by the fact the lineage affected by the gene defect, B cell in XLA and T and B cells in XSCID, use only the X chromosome that did not carry the defective gene as the active X chromosome.

In XLA, the failure of pre-B cells to differentiate into B cells may be due to a defect intrinsic to the B cell lineage or may be the result of an abnormality in another cell type that is required for normal B cell differentiation, such as cells in the bone marrow microenvironment, or cells that produce essential growth or differentiation factors.

To distinguish between these two possibilities, two women who were heterozygous for XLA and also heterozygous for another X-linked trait, the alleles of glucose-6-phosphate dehydrogenase (G6PD) were studied. Early in embryogenesis of the female, random inactivation of part of one X chromosome occurs in each somatic cell and is transmitted to all the descendants of that cell. See Lyon, "X-Chromosome Inactivation in Mammals", *Advances in Teratology* 1:25-54 (1966). Thus, in a woman who is heterozygous for an X-linked gene, on the average, half the cells in each tissue will express each allele. The exceptions to this mosaicism indicate origin from a common precursor, such as a monoclonal malignancy (Fialkow, "The Origin and Development of Human Tumors Studied with Cell Markers", *New England Journal of Medicine*, 291:26-35 (1974)), or a selective advantage of cells expressing the genes of one X chromosome over cells expressing genes on the other X. See Nyhan et al, "Hemizygous Expression of Glucose-6-Phosphate Dehydrogenase in Erythrocytes of Heterozygotes for the Lesch-Nyhan Syndrome", *Proc. Natl. Acad. Sci.*, 65:214"218 (1970): Migeon et al, "Adrenoleukodystrophy: Evidence for X Linkage, Inactivation, and Selection Favoring the Mutant Allele in Heterozygous Cells", *Proc. Natl. Acad. Sci.*, 78:5066-5070 (1981). If the gene defect in XLA were intrinsic to the B cell line, and the gene product were not transportable between cells, one would expect that B lineage cells from women heterozygous for a normal and an XLA gene might express only the X chromosome carrying the normal allele while other lineages would exhibit normal mosaicism. In our study of two women heterozygous for XLA and the $A^-$ and B enzyme activity, T cells and neutrophils exhibited approximately equal amounts of $A^-$ and B G6PD alleles, but B cells showed only the $A^-$ allele.

Cell Separation

Venous blood was anticoagulated with EDTA and then separated into erythrocytes, neutrophils and mononuclear cells by dextran sedimentation followed by Ficoll-Hypaque centrifugation. For further lymphocyte analysis, Ficoll-Hypaque separated lymphocytes were divided into T cells and T depleted cells by aminoethylisothiouronium bromide hydrobromide-treated sheep red blood cell (AET-SRBC) rosetting techniques. See Conley et al, "In Vitro Regulation of IgA Subclass Synthesis. II the Source of $IgA_2$ Plasma Cells", *J. of Immunol.*, 133:2312-2316 (1984). The T depleted fraction was indirectly stained for the B cell marker B1 as previously described. See Conley, "B Cells in Patients with X-Linked Agammaglobulinemia", *J. of Immunol.*, 134:3070-3074 (1985). To stain cells for the OKT8 marker, T cells were incubated on ice for 15 minutes with culture supernatant containing murine monoclonal antibody specific for the OKT8 antigen (the cell line was obtained from American Tissue Culture, Camden, N.J.). The cells were washed, then stained with fluorescein-labelled goat anti-mouse immunoglobulin (Southern Bio Technology, Birmingham, Ala.). Cells were sorted on a fluorescence-activated cell sorter (FACS) (B.D. FACS IV, Mountain View, Calif.). Cells that were positive and negative for each marker were reanalyzed by FACS after the sort and found to be greater than 97% of homogeneous with respect to the relevant marker.

Cell Cultures

T-cell colonies were derived from AET-SRBC rosetted lymphocytes preincubated with PHA then cultured for 7 days on soft agar in the presence of PHA and T cell growth factor as described. See Singer et al, "Single or Multicellular Origin of Human T Lymphocyte Colonies in Vitro: Modification by 12-0-Tetradecanoylphorbol 13-Acetate (TPA)", *J. of Immunol.*, 126:1390-1392 (1981).

Epstein-Barr virus transformed B-cell lines were established by culturing T-cell depleted mononuclear cells in microtiter wells with filtered supernatant from the Epstein-Barr virus producing cell line MCUV as described and cytogenetic studies were performed as described. See Raskind et al, "Evidence for a Multistep Pathogenesis of Myelodysplastic Syndrome", *Blood,* 63:1318–1323 (1984).

G6PD Analysis

Cellulose-acetate electrophoresis of cell lysates was done as described. See Singer et al, "Single or Multicellular Origin of Human T Lymphocyte Colonies in Vitro: Modification by 12-0-Tetradecanoylphorbol 13-Acetate (TPA)", *J. of Immunol.,* 126:1390–1392 (1981); and Raskind et al, "Evidence for a Multistep Pathogenesis of Myelodysplastic Syndrome", *Blood,* 63:1318–1323 (1984). The method used allows detection of a minor enzyme component constituting 5% or less of the total enzyme activity.

Results

Hypogammaglobulinemia was diagnosed in two black male cousins who had repeated bacterial infections in the first few years of life. Physical examination demonstrated unusually small lymph nodes. Fewer than 1% of the patients' peripheral blood lymphocytes were B cells (normal 5-15%). These findings suggested a diagnosis of X-linked agammaglobulinemia. This diagnosis was supported by examination of the pedigree.

The mothers of both affected boys (II-3 and II-4) had normal concentrations of serum immunoglobulin, normal numbers of B cells, (10%, and 13% of peripheral blood lymphocytes respectively,) and normal X chromosomes by karyotype analysis. Analysis of G6PD enzymes on erythrocyte and leukocyte lysates from members of this family demonstrated that both mothers were heterozygous for the $A^-$ and B alleles of G6PD. One affected boy inherited the $A^-$ allele and the other inherited the B allele, indicating a crossover between the genes for XLA and G6PD in one of the two boys.

Peripheral blood cells from both mothers were separated into red cells, neutrophils and mononuclear cells. Approximately equal amounts of $A^-$ and B G6PD activities were found in the neutrophils and mononuclear cells but only B G6PD could be detected in red cells, suggesting that both women carry the $A^-$ variant allele. The $A^-$ variant, which is present in approximately 15% of black women, has the same electrophoretic mobility and enzyme activity as the A enzyme but is rapidly degraded in non-nucleated cells, such as red blood cells. See Yoshida et al, "Negro Variant of Glucose-6-Phosphate Dehydrogenase Deficiency ($A^-$) in Man", *Science,* 155:97–99 (1967).

Although mononuclear cells exhibited equal amounts of the $A^-$ and B enzyme activities, the possibility that a lymphocyte subset might demonstrate unbalanced expression of the G6PD alleles could not be excluded. To examine this possibility, mononuclear cells were separated into T cells and non-T cells (B cells ) by allowing the T cells to rosette with AET treated sheep red blood cells. The T cells were preincubated in PHA then cultured at low cell density in semi-soft agar containing PHA and IL-2. After 7 days, the colonies were pooled, then analyzed. Lysates from T cell colonies from both women contained equal amounts of the $A^-$ and B enzyme.

The T depleted fraction of lymphocytes was incubated with Epstein-Barr virus, washed, then divided into multiple aliquots to permit the growth of many Epstein-Barr virus transformed B-cell lines. After 6–8 weeks 51 B0cell lines from II-3 and 71 B cell lines from II-4 could be analyzed individually. All B cell lines from II-3 and 69 of 71 lines from II-4 exhibited only $A^-$ G6PD. In the remaining two lines, a small amount of B G6PD activity may have been present (less than 5%).

The unbalanced expression of G6PD alleles in B-cell lines but not in T cells suggested that the gene defect in XLA was intrinsic to the B cell lineage and did not influence survival of T cells. However, in vitro growth of lymphocytes represents the expansion of a subset of total lymphocytes. This subset may not be representative of the entire cell population. Therefore, freshly separated lymphocytes were divided into T cells and T depleted cells. The T cell population was stained by indirect immunofluorescent staining techniques for the T cytotoxic/suppressor cell marker, OKT8, and divided into T8 positive and T8 negative cells by fluorescence-activated cell sorting. The T depleted cells were stained with B1, a B cell specific monoclonal antibody, and sorted into B1-positive and B1 negative cell lysates. However, the B1-positive cell lysates from both women contained only $A^-$ enzyme activity.

The data thus demonstrate that the gene defect in X-linked agammaglobulinemia is intrinsic to the B cell lineage. Neutrophils, E-rosette forming T cells, T cells expressing the OKT8 cytotoxic/suppressor cell phenotype and T cell colonies manifested approximately equal amount of $A^-$ and B G6PD in two women who were heterozygous for both XLA and G6PD. In marked contrast, B cells and Epstein-Barr virus transformed B cell lines expressed a single allele almost exclusively, the allele on the X chromosome that was not carrying the gene for XLA.

If the XLA gene product were derived from cells other than B cells, such as T cells or cells of the bone marrow microenvironment, then the cells with the normal XLA gene on the active X chromosome could provide the substance necessary for the differentiation of the B cell precursors in which the mutant was on the active X chromosome. In a like fashion, if the XLA gene product were produced by B cells and were transportable between cells, B cell precursors expressing either X chromosome could be induced to differentiate, and mature B cells should develop from both G6PD $A^-$ and G6PD B producing precursors in subjects II-3 and II-4. The finding of expression of essentially a single G6PD allele in uncultured and transformed B cells strongly supports the hypothesis that normal function of the XLA gene is required in each developing B cell in order for B cell differentiation to proceed.

Subtle T cell abnormalities have been reported in patients with X-linked agammaglobulinemia. For example, an increased proportion of T cells from these patients express a marker seen on immature T cells (Tedder, et al, "Evaluation of Lymphocyte Differentiation in Primary and Secondary Immunodeficiency Diseases", *J. of Immunol.,* 135:1786–1791 (1985)) and activity of the enzyme ecto-5'-nucleotidase is decreased in T cells from patients compared to normal T cells. See Thompson et al, "Ecto-5'-Nucleotidase Activity in Lymphoblastoid Cell Lines Derived from Heterozygotes for Congenital X-Linked Agammaglobulinemia", *J. of Immunol.,* 125:190–193 (1980). These findings can be interpreted as indicating that the genetic defect in XLA affects T cells as well as B cells or as indicating that normal maturation of T cells is influenced by B cells. Our findings suggest that the latter hypothesis is more likely to be correct.

Pedigree studies have demonstrated that the locus for XLA is not measurably linked to the locus for the Xg blood group (Sanger et al, "The Xg Blood Groups and Familial Hypogammaglobulinemia", *Lancet*, 1:859–860 (1963); Rosen et al "The Xg Groups and Congenital Hypgammaglobulinemia", *Vox Sang.*, 10:729–730 (1965); Mensink et al, "X-Linked Agammaglobulinemia and the Red Blood Cell Determinants Xg and 12E7 Are Not Closely Linked", *Hum. Genet.*, 68:303–309 (1984)), which is on the distal portion of the short arm of the X chromosome. The locus for G6PD is at the distal end of the long arm of the X chromosome and the demonstration of the recombination for the G6PD and XLA genes in one of the two informative individuals in our study suggests that these two loci are also not closely linked. Preliminary evidence places the XLA locus near the centromere (Schuurman et al, "X-Linked Agammaglobulinemia: Mapping of the Gene for XLA Carrier Detection", *Ped. Res.*, 19:1072 (Abstract) (1985); Belmont et al, "Regional Mapping of X-Linked Agammaglobulinemia", *Am. J. Human Gen.*, 37:A140 (Abstract) (1985)), or on the proximal portion of the long arm of the X chromosome.

The genetic defect responsible for X-linked agammaglobulinemia is thus intrinsic to the B cell lineage. In the heterozygous female this gene defect results in a failure of differentiation of B cell precursors expressing defective allele.

Based on the above findings, it was then predicted that lymphocytes from a carrier of X-linked severe combined immunodeficiency disease (XSCID) might show preferential inactivation of the X chromosome bearing the SCID mutation. In accordance with the preferred techniques of the present invention, hamster/human hybrids retaining the active X from T and B cells isolated from a carrier of an X-linked SCID were analyzed by Southern Blot for an X chromosome restriction fragment length polymorphism (RFLP) for which the carrier female was heterozygous. The techniques used were those of Nussbaum et al, cited above, which has been incorporated by reference as if fully set forth herein.

In contrast to random X chromosome inactivation in 11 hybrids made from a control female's lymphocytes (5 had 1 allele, 4 had the other, and two had both), 17 hybrids from the SCID carrier's T cells and 7 from her B cells had only 1 RFLP allele (p less than 0.008 for B cells and less than 0.0000001 for T cells). Thus the only T cells and the only B cells present in carrier peripheral blood are those in which the SCID gene is on the inactive X. Because RFLP's are available to distinguish virtually any two X chromosomes, RFLP analysis of hybrids is thus a powerful method for determining the carrier status of all females at risk for transmitting SCID as well as other X-linked disorders.

More particularly, the use of somatic cell hybrids is important to the method of the present invention because only a small minority of women at risk for carrying X-linked immune diseases can be expected to be heterozygous for other markers, such as G6PD. To allow distinction of the active and inactive X chromosomes in all women at risk, the cell fusion techniques and DNA probes are particularly useful. When blood lymphocytes from a female are transfused with a Chinese hamster cell line, such as RJK88, in which the X-linked gene for the enzyme for hypoxanthine phosphoribo-syltransferase (HPRT) has been deleted, growth in hypoxanthine/azaserine or HAT medium following fusion will result in cell death except for fusion products which have retained the active human X chromosome to provide the HPRT. The HPRT on the inactive human X does not become reactivated. See Wieaker et al, "X Inactivation Patterns in Two Syndromes with Probably X-Linked Dominant Male Lethal Inheritance", *Clinical Genetics*, 28:238–242 (1985) and Mohandas et al, "Reactivation of an Inactive Human X Chromosome: Evidence for X Inactivation by DNA Methylation", *Science*, 211:393–396 (1981). During growth in this medium, the rapid mitosis of the subject hybrid cell line tends to result in the elimination of human chromosomes. Thus, most hybrid colonies will spontaneously lose the inactive human X while retaining the active human X to provide HPRT. If desired, subcloned cells may be exposed to 6-thioguanine to select for hybrids which have lost their HPRT activity. In any event, DNA prepared from these hybrids is analyzed for the presence of an X chromosome restriction fragment length polymorphism (RPLP), a normal variation in the pattern of DNA fragments seen in Southern Blot hybridization of genetic DNA digested with a restriction endonuclease. Because over 100 RFLP probes are currently available for the X chromosome, virtually every female is heterozygous for at least one RFLP.

What is claimed is:

1. A method of diagnosing a human female suspected of being an symptomatic carrier of X-linked agammaglobulinemia (XLA), comprising the steps of:
   (a) sampling B cell lymphocytes of said female; and
   (b) determining whether at least 95% of said B cell lymphocytes exhibit inactivation of the same chromosome; whereby said X chromosome inactivation is diagnostic of the likelihood that said female is an asymptomatic carrier of XLA.

2. The method of claim 1 wherein said determining step comprises first separating the active from the inactive X chromosomes.

3. The method of claim 2 wherein said separating step comprises forming a somatic hybrid cell line with said B cell lymphocytes.

4. The method of claim 3 wherein said hybrid cell line is a hamster/human hybrid cell line.

5. The method of claim 4 wherein said hybrid cell line is cultured in a medium which selects for the presence of either one of the X chromosomes.

6. The method of claim 5 wherein the identity of the X chromosome is determined by digesting X chromosome DNA with a restriction endonuclease to form DNA fragments and subjecting said fragments to a Southern Blot test.

7. A method of screening a human female suspected of being an asymptomatic carrier of X-linked severe combined immunodeficiency (XSCID), comprising the steps of:
   (a) sampling the B or T cell lymphocytes of said female; and
   (b) determining whether at least 85% of said lymphocytes exhibit inactivation of the same chromosome; whereby said X chromosome inactivation is associated with XSCID.

8. The method of claim 7 wherein said determining step comprises first separating the active from the inactive X chromosomes.

9. The method of claim 8 wherein separating step comprises forming a somatic hybrid cell line with said B or T cell lymphocytes.

10. The method of claim 9 wherein said hybrid cell line hamster/human hybrid cell line.

11. The method of claim 10 wherein said hybrid cell line is cultured in a medium which selects for the presence of either one of the X chromosomes.

12. The method of claim 11 wherein the identity of the X chromosome is determined by digesting X chromosome DNA with a restriction endonuclease to form DNA fragments and subjecting said fragments to a Southern Blot test.

* * * * *

UNITED STATES PATENT AND TRADEMARK OFFICE
CERTIFICATE OF CORRECTION

PATENT NO. : 5,106,728

DATED : April 21, 1992

INVENTOR(S) : Mary E. Conley, Robert L. Nussbaum & Jennifer M. Puck

It is certified that error appears in the above-identified patent and that said Letters Patent is hereby corrected as shown below:

On the title and col. 1 line 1,
In the title, [54], first line, change "CALLIER" to --CARRIER--.

Signed and Sealed this

Twenty-third Day of November, 1993

Attest:

BRUCE LEHMAN

Attesting Officer   Commissioner of Patents and Trademarks

UNITED STATES PATENT AND TRADEMARK OFFICE
CERTIFICATE OF CORRECTION

| | |
|---|---|
| PATENT NO. : | 5,106,728 |
| DATED : | April 21, 1992 |
| INVENTOR(S) : | Mary E. Conley, Robert L. Nussbaum & Jennifer M. Puck |

It is certified that error appears in the above-indentified patent and that said Letters Patent is hereby corrected as shown below:

In column 1, before BACKGROUND OF THE INVENTION, please make reference to the following Government Grant information:

This work was supported in part by National Institute of Health, grant numbers A121477, CA15822 and HD0067. The United States government may have certain rights in this invention Signed and Sealed this Thirteenth Day of October 1998

Attest:

BRUCE LEHMAN

Attesting Officer

Commissioner of Patents and Trademarks